US009443002B1

(12) United States Patent
Freese et al.

(10) Patent No.: US 9,443,002 B1
(45) Date of Patent: Sep. 13, 2016

(54) DYNAMIC DATA ANALYSIS AND SELECTION FOR DETERMINING OUTCOMES ASSOCIATED WITH DOMAIN SPECIFIC PROBABILISTIC DATA SETS

(71) Applicant: Grand Rounds, Inc., San Francisco, CA (US)

(72) Inventors: Nate Freese, San Francisco, CA (US); Owen Tripp, San Francisco, CA (US); Evan Richardson, San Francisco, CA (US)

(73) Assignee: Grand Rapids, Inc., San Francisco, CA (US)

( * ) Notice: Subject to any disclaimer, the term of this patent is extended or adjusted under 35 U.S.C. 154(b) by 0 days.

(21) Appl. No.: 14/796,946

(22) Filed: Jul. 10, 2015

(51) Int. Cl.
*G06F 15/18* (2006.01)
*G06F 17/30* (2006.01)
*G06N 7/00* (2006.01)

(52) U.S. Cl.
CPC ..... *G06F 17/30598* (2013.01); *G06F 17/3053* (2013.01); *G06N 7/005* (2013.01)

(58) Field of Classification Search
None
See application file for complete search history.

(56) References Cited

U.S. PATENT DOCUMENTS

| | | | | |
|---|---|---|---|---|
| 7,657,540 B1 * | 2/2010 | Bayliss | ................. | G06Q 10/10 707/609 |
| 2006/0149821 A1 * | 7/2006 | Rajan | ................... | G06Q 10/107 709/206 |
| 2007/0038705 A1 * | 2/2007 | Chickering | ............. | H04L 51/12 709/206 |
| 2009/0043593 A1 * | 2/2009 | Herbrich | ............ | G06Q 30/0185 705/318 |
| 2011/0313548 A1 * | 12/2011 | Taylor | ............... | G06F 17/30958 700/47 |

OTHER PUBLICATIONS

Breiman, Leo. "Random forests." Machine learning 45.1 (2001): 5-32.*
Zhu, Ji, et al. "Multi-class adaboost." Statistics and its Interface 2.3 (2009): 349-360.*

* cited by examiner

*Primary Examiner* — Kakali Chaki
*Assistant Examiner* — Daniel Pellett
(74) *Attorney, Agent, or Firm* — Finnegan, Henderson, Farabow, Garrett & Dunner, LLP

(57) ABSTRACT

Computer-implemented systems and methods are disclosed for analyzing and selecting data to estimate the potential weight associated with an event. The systems and methods provide for obtaining data sets associated with a first event and events that can result from the first event, classifying the data into weight data related to a weight associated with the resulting events and probability data related to the probability that the resulting events will occur, prioritizing the data based on the availability the data sets, prioritizing the probability data based on a statistical analysis of the relevance of the probability data, analyzing the prioritized weight data to establish weight estimates for the resulting events, analyzing the prioritized probability data to establish probability estimates for the resulting events, and providing for display a decision tree with the established weight estimates and probability estimates.

18 Claims, 7 Drawing Sheets

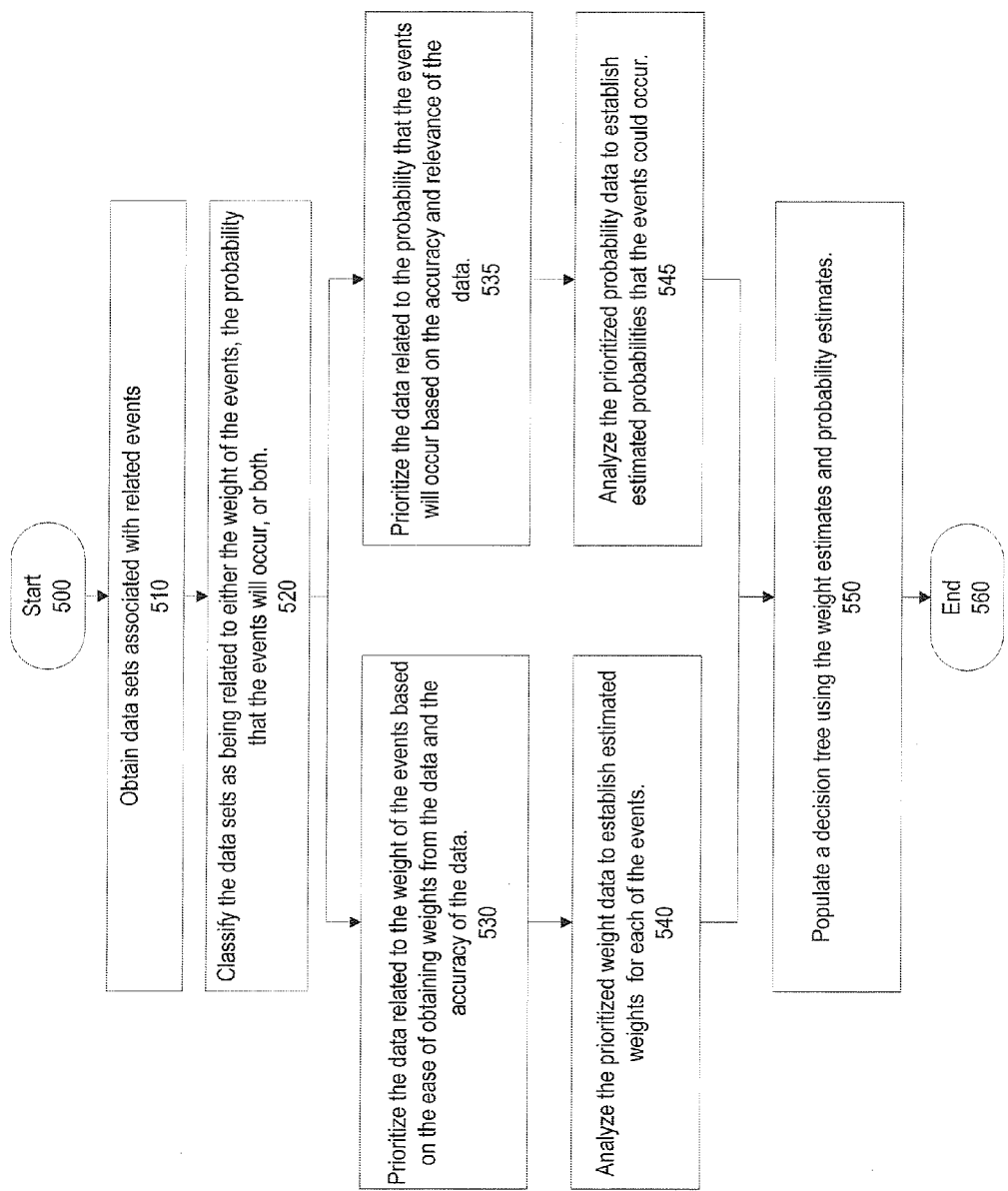

DYNAMIC DATA ANALYSIS AND SELECTION FOR DETERMINING OUTCOMES ASSOCIATED WITH DOMAIN SPECIFIC PROBABILISTIC DATA SETS

BACKGROUND

An ever increasing amount of data and data sources are now available to researchers, analysts, organizational entities, and others. This influx of information allows for sophisticated analysis but, at the same time, presents many new challenges for sifting through the available data and data sources to locate the most relevant and useful information. As the use of technology continues to increase, so, too, will the availability of new data sources and information.

Various methods can be used for analyzing data. Decision trees, one such method, provide a mechanism for evaluating the future result or outcome of multiple different choices or courses of action. To be effective, however, decision trees must be populated with data appropriate to the circumstances and goals of a particular domain. Furthermore, the data used must provide enough accuracy to ensure that predicted eventualities sufficiently model realized outcomes. The tolerance for accuracy of the predictions is highly dependent on the domain and goals of a particular application.

Because of the abundant availability of data from a vast number of data sources, determining the optimal values and sources for use in analytic methods, such as decision trees, presents a complicated problem that is difficult to overcome. The analysis obtained through a decision tree is only as effective as the data used to populate the various metrics under analysis. Accurately utilizing the available data can require both a team of individuals possessing extensive domain expertise as well as many months of work to create useful decision tree models detailing possible outcomes. The process can involve exhaustively searching existing literature, publications, and other available data to identify and study relevant data sources that are available both privately and publicly.

While this approach can often provide effective academic analysis, applying these types of analytical techniques to domains requiring accurate results obtainable only through time and resource intensive research is incompatible with the demands of modern applications. For example, the developed model may not line up with specific circumstances or individual considerations. In this scenario, applying the model requires extrapolation to fit the specific circumstances, diluting the effectiveness of the model, or requires spending valuable time and resources to modify the model. As a result, models developed in this way typically provide only generalized guidance insufficient for use in individualized settings. As more detailed and individualized data becomes available, demand for the ability to accurately discern relevant data points from the sea of available information and efficiently apply that data across thousands of individualized scenarios increases.

BRIEF DESCRIPTION OF THE DRAWINGS

Reference will now be made to the accompanying drawings showing example embodiments of this disclosure. In the drawings:

FIG. 5 is a flowchart of an exemplary method for evaluating data sources, consistent with embodiments of the present disclosure.

DETAILED DESCRIPTION

Reference will now be made in detail to the exemplary embodiments implemented according to the present disclosure, the examples of which are illustrated in the accompanying drawings. Wherever possible, the same reference numbers will be used throughout the drawings to refer to the same or like parts.

The embodiments described herein provide technologies and techniques for evaluating large numbers of data sources and vast amounts of data used in the creation of a predictive or analytical data model. These technologies can use information relevant to the specific domain and application of a data model to prioritize potential data sources. Further, the technologies and techniques herein can interpret the available data sources and data to extract probabilities and outcomes associated with the specific domain and application of the data model. The described technologies can synthesize the data into a coherent data model, such as a decision tree, that can be used to analyze and compare various paths or courses of action.

These technologies can efficiently evaluate data sources and data, prioritize their importance based on domain and circumstances, and provide effective and accurate predictions that can be used to evaluate potential courses of action. The technologies and methods allow for the application of data models to individual circumstances. These methods and technologies allow for detailed evaluation that can improve decision making on a case by case basis.

The embodiments described herein can apply to many fields. Descriptions and applications related to specific domains do not preclude the application of the described embodiments to other technologies of fields.

Figure 1:
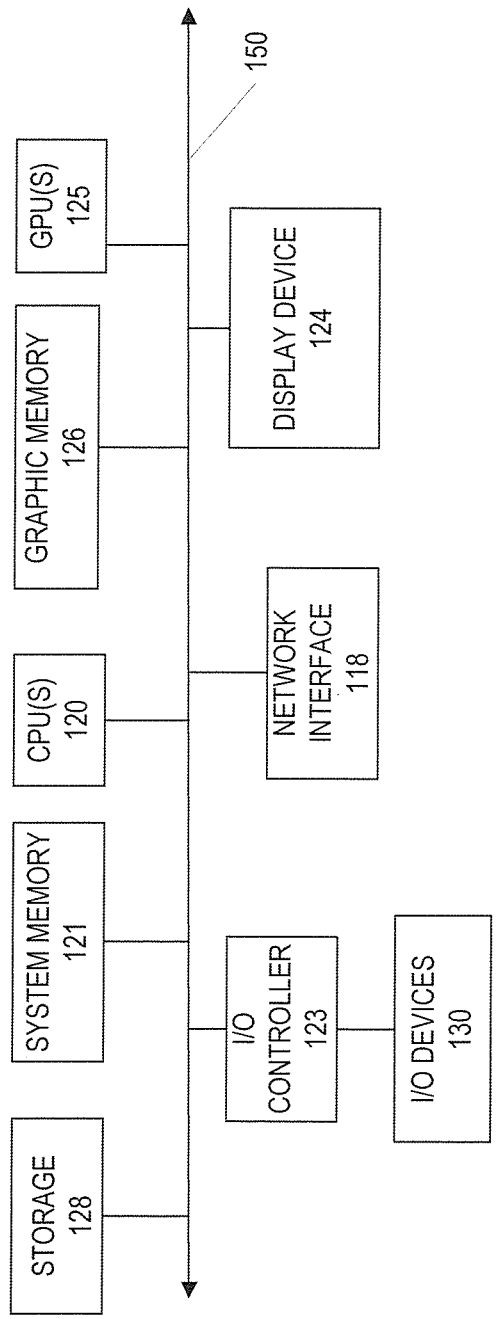
FIG. 1 is a block diagram of an exemplary computing device, consistent with embodiments of the present disclosure.

FIG. 1 is a block diagram of an exemplary computing device 100, consistent with embodiments of the present disclosure. In some embodiments, computing device 100 can be a server providing the functionality described herein. Further, computing device 100 can be a second device providing the functionality described herein or receiving information from a server to provide at least some of that information for display.

Computing device 100 can include one or more central processing units (CPUs) 120 and system memory 121. Computing device 100 can also include one or more graphics processing units (GPUs) 125 and graphic memory 126. CPUs 120 can be single or multiple microprocessors, field-programmable gate arrays, or digital signal processors capable of execution sets of instructions stored in a memory (e.g., system memory 121), a cache, or a register. CPUs 120 can contain one or more registers for storing variable types of data including, inter alia, data, instructions, floating point values, conditional values, memory addresses for locations in memory (e.g., system memory 121 or graphic memory 126), pointers and counters. CPU registers can include special purpose registers used to store data associated with executing instructions such as an instruction pointer, instruction counter, and/or memory stack pointer. System memory 121 can include a tangible and/or non-transitory computer-readable medium, such as a flexible disk, a hard disk, a compact disk read-only memory (CD-ROM), magneto-optical (MO) drive, digital versatile disk random-access memory (DVD-RAM), a solid-state disk (SSD), a flash drive and/or flash memory, processor cache, memory register, or a semiconductor memory. System memory 121 can be one or more memory chips capable of storing data and allowing direct access by CPUs 120. System memory 121 can be any type of random access memory (RAM), or other available memory chip capable of operating as described herein.

CPUs 120 can communicate with system memory 121 via a system interface 150, sometimes referred to as a bus. GPUs 125 can be any type of specialized circuitry that can manipulate and alter memory (e.g., graphic memory 126) to provide and/or accelerate the creation of images. GPUs 125 can store images in a frame buffer for output to a display device such as display device 124. GPUs 125 can have a highly parallel structure optimized for processing large, parallel blocks of graphical data more efficiently than general purpose CPUs 120. Furthermore, the functionality of GPUs 125 can be included in a chipset of a special purpose processing unit or a co-processor.

CPUs 120 can execute programming instructions stored in system memory 121 or other memory, operate on data stored in memory (e.g., system memory 121) and communicate with GPUs 125 through the system interface 150, which bridges communication between the various components of computing device 100. In some embodiments, CPUs 120, GPUs 125, system interface 150, or any combination thereof, are integrated into a single chipset or processing unit. GPUs 125 can execute sets of instructions stored in memory (e.g., system memory 121), to manipulate graphical data stored in system memory 121 or graphic memory 126. For example, CPUs 120 can provide instructions to GPUs 125, and GPUs 125 can process the instructions to render graphics data stored in the graphic memory 126. Graphic memory 126 can be any memory space accessible by GPUs 125, including local memory, system memory, on-chip memories, and hard disk. GPUs 125 can enable displaying of graphical data stored in graphic memory 126 on display device 124.

Computing device 100 can include display device 124 and input/output (I/O) devices 130 (e.g., a keyboard, a mouse, or a pointing device) connected to I/O controller 123. I/O controller 123 can communicate with the other components of computing device 100 via system interface 150. It is appreciated that CPUs 120 can also communicate with system memory 121 and other devices in manners other than through system interface 150, such as through serial communication or direct point-to-point communication. Similarly, GPUs 125 can communicate with graphic memory 126 and other devices in ways other than system interface 150. In addition to receiving input, CPUs 120 can provide output via I/O devices 130 (e.g., through a printer, speakers, or other output devices).

Furthermore, computing device 100 can include a network interface 118 to interface to a LAN, WAN, MAN, or the Internet through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. Network interface 118 can comprise a built-in network adapter, network interface card, PCMCIA network card, card bus network adapter, wireless network adapter, USB network adapter, modem or any other device suitable for interfacing computing device 100 to any type of network capable of communication and performing the operations described herein.

Figure 2:
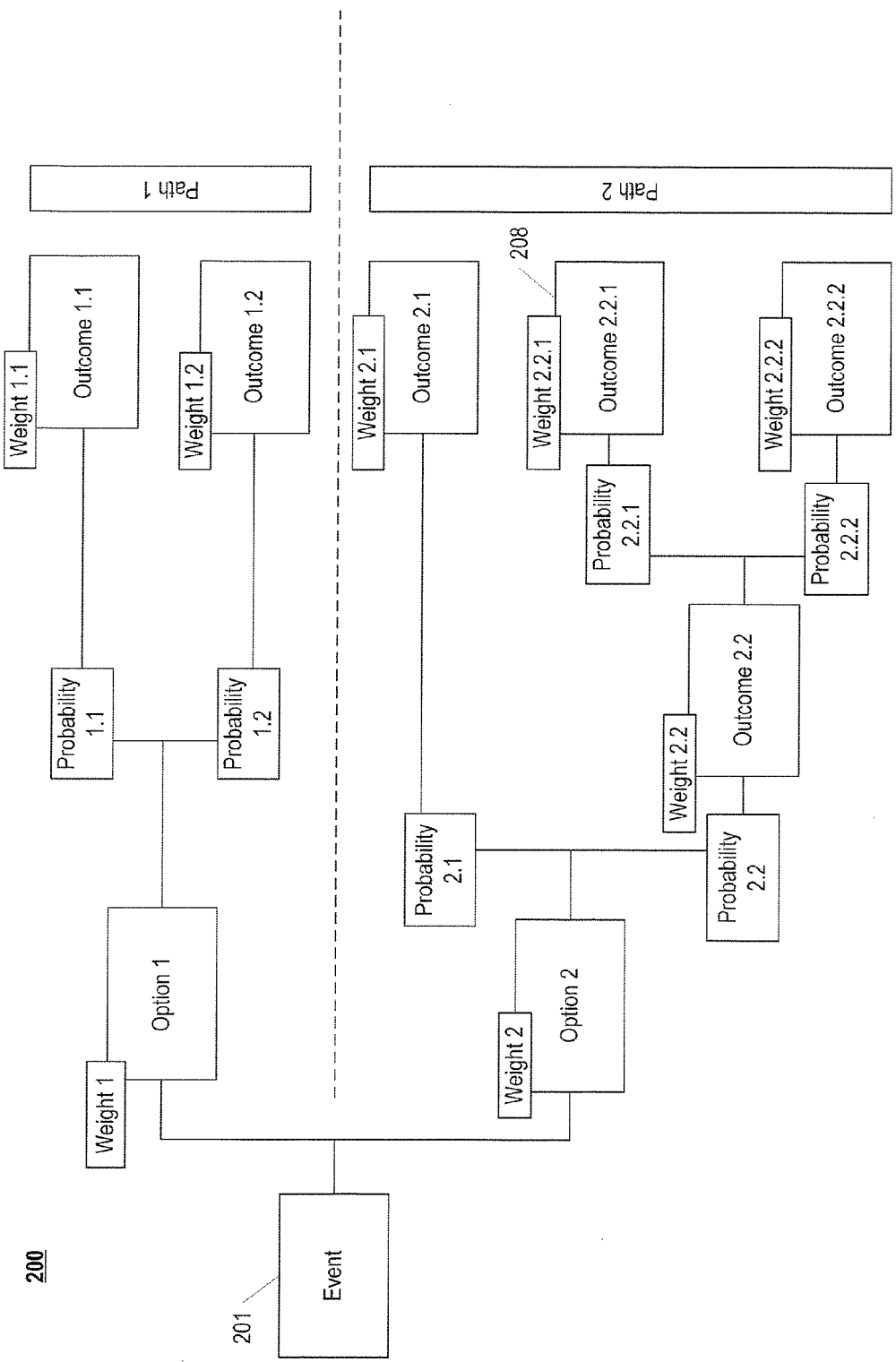
FIG. 2 is an exemplary analytic model consistent with embodiments of the present disclosure.

FIG. 2 is a representation of an exemplary analytic model 200 consistent with embodiments of the present disclosure. Analytic model 200 can represent a decision tree that includes two paths (e.g., path 1 and path 2) for responding to an initial event (e.g., event 201). Event 201 can represent anything for which there can be multiple responses or courses of action. A decision tree, such as decision tree 200, can assist with comparing the expected outcomes related to each potential option and assisting with conclusions regarding which path should be followed.

Decision tree 200 can represent multiple options or actions following the event. For example one can respond to event 201 following either option 1 or option 2. While decision tree 200 only demonstrates two options (e.g., option 1 and option 2), it is appreciated that decision tree 200 can include as many options (and corresponding outcomes) as are possible. Further, option 1 and option 2 can represent all possible options for responding to event 201 and/or only a subset of all possible options for responding to event 201.

Each option can further result in additional outcomes that, together with the option, represent the entirety of possible outcomes for a specific path or course of action. For example, option 1 can result in outcome 1.1 and outcome 1.2, that, together with option 1, can represent all possible outcomes of path 1. Further, option 2 can result in outcome 2.1 and outcome 2.2. Outcome 2.2 can further result in additional outcomes 2.2.1 and 2.2.2. Outcomes 2.1, 2.2, 2.2.1, and 2.2.2 together with option 2 can represent the entirety of path 2. Just as option 1 and option 2 can represent all or only a subset of possible options for responding to event 201, outcomes 1.1, 1.2, 2.1, 2.2, 2.2.1, and 2.2.2 can represent all or only a subset of possible outcomes resulting from their respective options and/or outcomes.

Options, outcomes, and their child outcomes can occur in more than one path (e.g., path 1 and path 2). In some embodiments, outcome 2.2 is the same as option 1. Further, in these embodiments, outcomes 1.1 and 1.2 are the same as outcomes 2.2.1 and 2.2.1. This example demonstrates that an option or outcome on one path can also exist as part of another path. Further, this example represents that even though different options can be followed, there are scenarios where following one option can lead to the same set of outcomes in a second option although those outcomes can occur at different times or under different circumstances.

Additionally, each potential option and/or outcome can include a weight. The weight can be any metric or value that is associated in some way with the option or outcome. The metric can be domain specific and can represent any value useful for comparing outcomes and/or options. In some domains higher values can be favored, and, in some domains, lower values can be preferred. Weights can be directly related to the specific option or outcome. For example weight 1 can be a value or metric associated with option 1. Similarly weights 1.1 and 1.2 can be associated with outcomes 1.1 and 1.2 respectively. Further, in this example, weight 2 can be associated with option 2, weights 2.1 and 2.2 can be associated with outcomes 2.1 and 2.2 respectively, and weights 2.2.1 and 2.2.2 can be associated with outcomes 2.2.1 and 2.2.2 respectively. Each weight can be independent from its predecessor outcome or option. For example, weight 2.2.1, associated with outcome 2.2.1, can be entirely independent from outcome 2.2 and weight 2.2, despite the relationship between the two outcomes. In some embodiments, weight 2.2.1 is affected by outcome 2.2.

In addition to weights, each outcome can be associated with a probability that can represent the relative probability of that event occurring. For example, probability 1.1 can be the probability that outcome 1.1 will follow option 1. Similarly, probability 1.2 can be the probability that outcome 1.2 will result from option 1. Similarly, probability 2.1 and probability 2.2 can represent the likelihood that outcome 2.1 and outcome 2.2, respectively, will result from option 2. Further, probability 2.2.1 and probability 2.2.2 can represent the probability that outcome 2.2.1 and outcome 2.2.2, respectively, can result from outcome 2.2.

Probabilities at each level and branch in the decision tree can be relative to other probabilities in that level and branch. For example, probability 2.2.1 can be relative to probability 2.2.2 but can be unassociated with probability 2.1 and 2.2. Accordingly, if outcome 2.2.1 and outcome 2.2.2 are the only possible outcomes of outcome 2.2, probability 2.2.1 and probability 2.2.2 can total 100%. Further, in this example, if outcome 2.1 and outcome 2.2 are the only possible outcomes of option 2, than probability 2.1 and probability 2.2 can total 100% also.

In some embodiments, there can be additional outcomes that are not considered. In these embodiments, the sum of probabilities can total less than 100%. For example, if outcome 2.2 can include a 5% probability of an additional outcome that is not represented on decision tree 200, than probability 2.2.1 and probability 2.2.2 will only total 95%.

After being populated with options (e.g., options 1 and 2), outcomes (e.g. Outcomes 1.1, 1.2, 2.1, 2.2, 2.2.1, and 2.2.2), weights (e.g., weights 1, 1.1, 1.2, 2, 2.1, 2.2, 2.2.1, and 2.2.2) and probabilities (e.g., probability 1.1, 1.2, 2.1, 2.2, 2.2.1, and 2.2.2), decision tree 200 can be used to analyze the respective paths (e.g., path 1 and path 2). By multiplying each weight with its respective probability, a probability adjusted value can be reached for every potential outcome for a path. For example multiplying weight 1.1 by probability 1.1 and weight 1.2 by probability 1.2 can result in an adjusted weight for outcome 1.1 and 1.2. Summing these adjusted weights can provide a total weight for path 1.

A similar calculation can be performed for path 2. Weight 2.1 can be multiplied with probability 2.1 to discern an adjusted weight for outcome 2.1. When multiple levels of outcomes are possible (e.g., option 2 can result in outcome 2.2, which in turn can result in outcomes 2.2.1 and 2.2.2) the probabilities leading to each final outcome can be multiplied together to determine an intermediate probability for that outcome. Further, each weight leading to that final outcome can be summed resulting in an intermediate weight for that outcome. For example, the adjusted probability for outcome 2.2.1 can be obtained by first multiplying probability 2.2.1 with probability 2.2 to determine the expected probability that outcome 2.2.1 can occur. Second, in this example, weight 2.2 and weight 2.2.1 can be summed to determine the total weight if outcome 2.2.1 occurs. Multiplying the expected probability by the total weight can result in the adjusted weight for outcome 2.2.1. Similar calculations can be made for outcome 2.2.2 and outcome 2.1 to determine adjusted weights for all three potential results of path 2. Summing these adjusted weights can result in a total weight for path 2. After total weights are determined for each path (e.g., path 1 and path 2) the weights can be compared to determine the path that would yield the most desired outcome based on the meaning of the total weights to the specific domain being analyzed.

It is appreciated that this type of analytical model can be applied to a variety of industries and circumstances. Subsequent figures and disclosure provide examples based on specific domains as an example of using a decision tree but are not intended to limit the application of the disclosure to that specific domain or industry. Further, the application and usefulness of a decision tree, such as decision tree 200, is driven by the quality and accuracy of the data used to populate the decision tree.

Figure 3A:
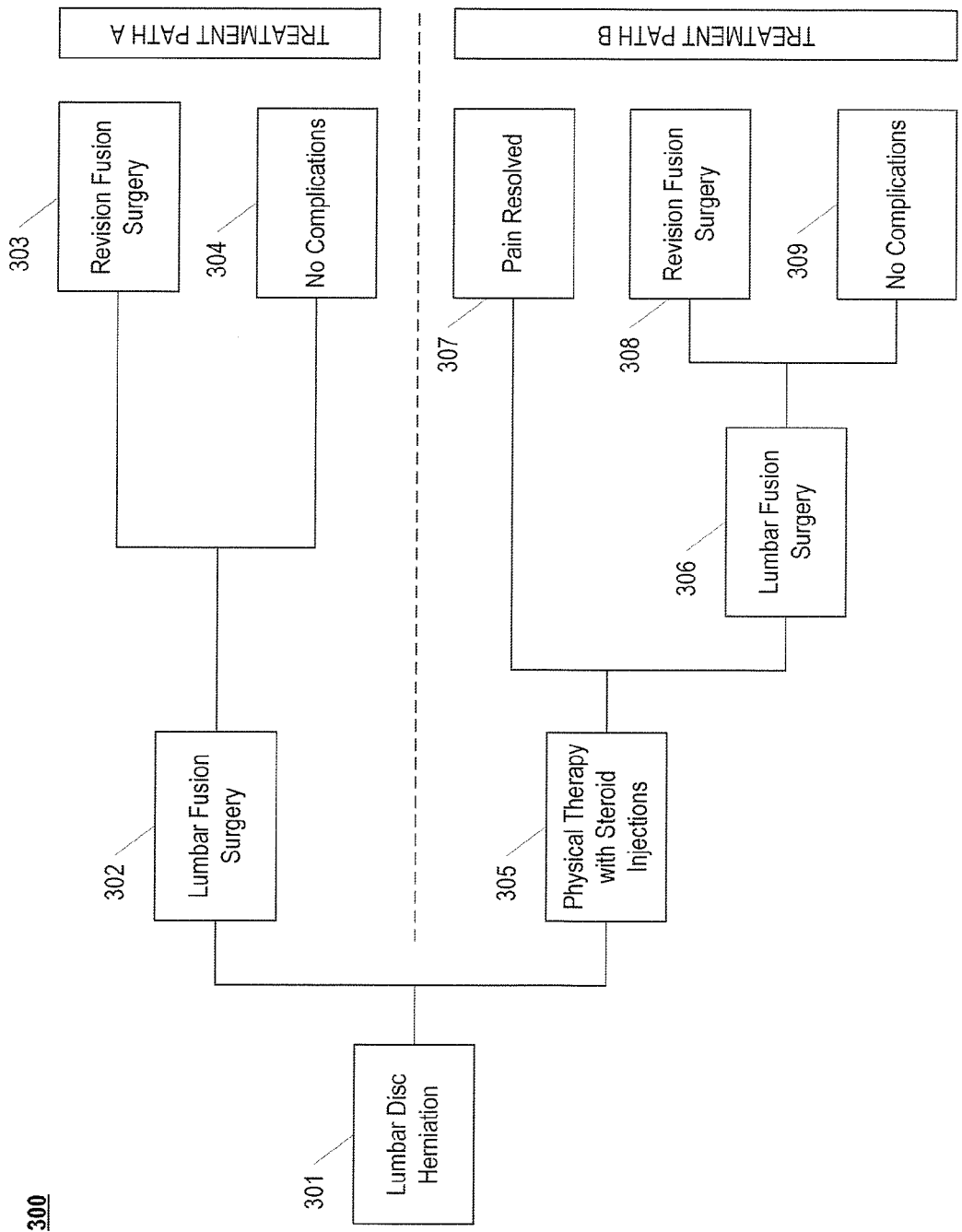
FIGS. 3A-3C are exemplary analytic models consistent with embodiments of the present disclosure.
Figure 3B:
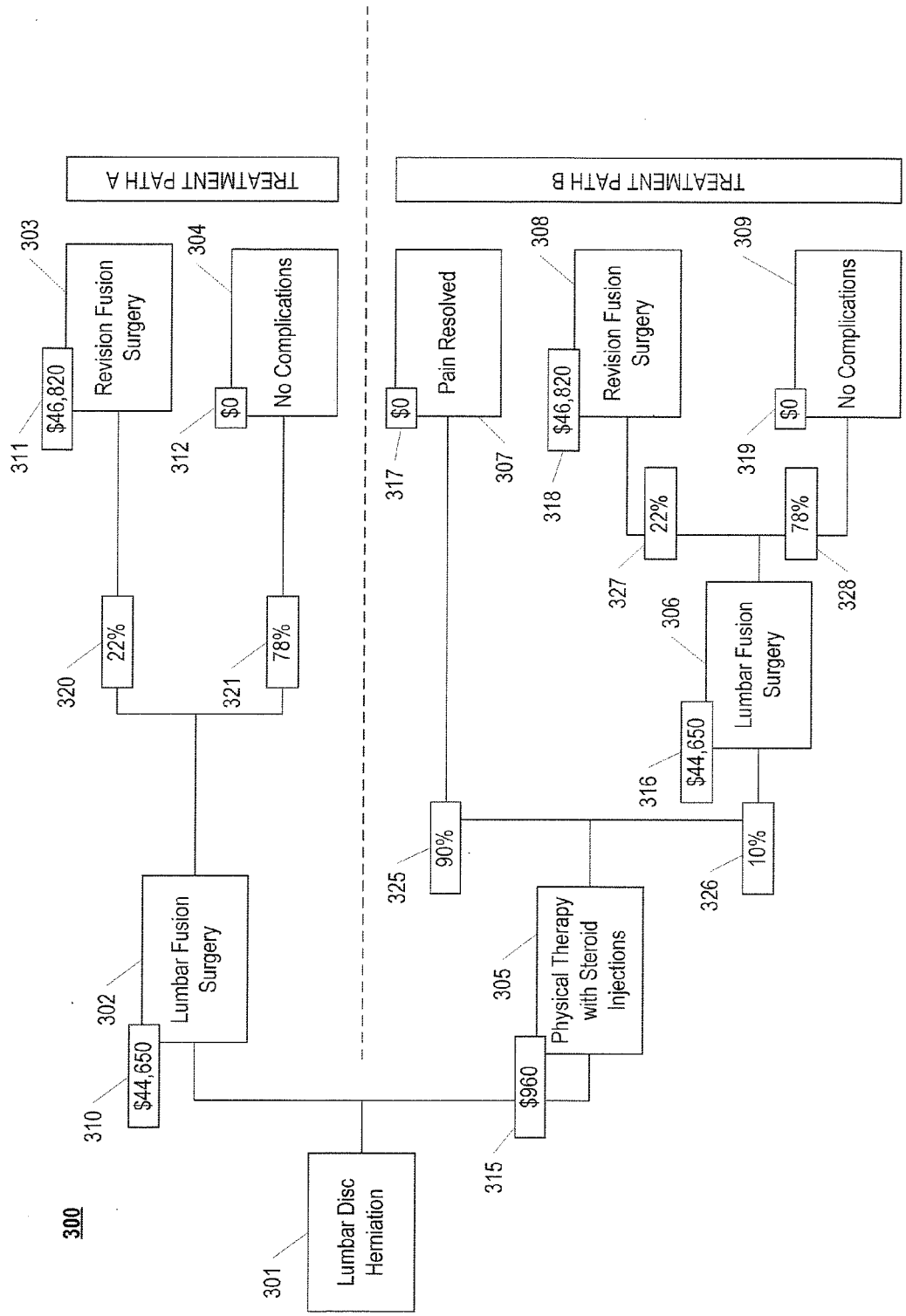
Figure 3C:
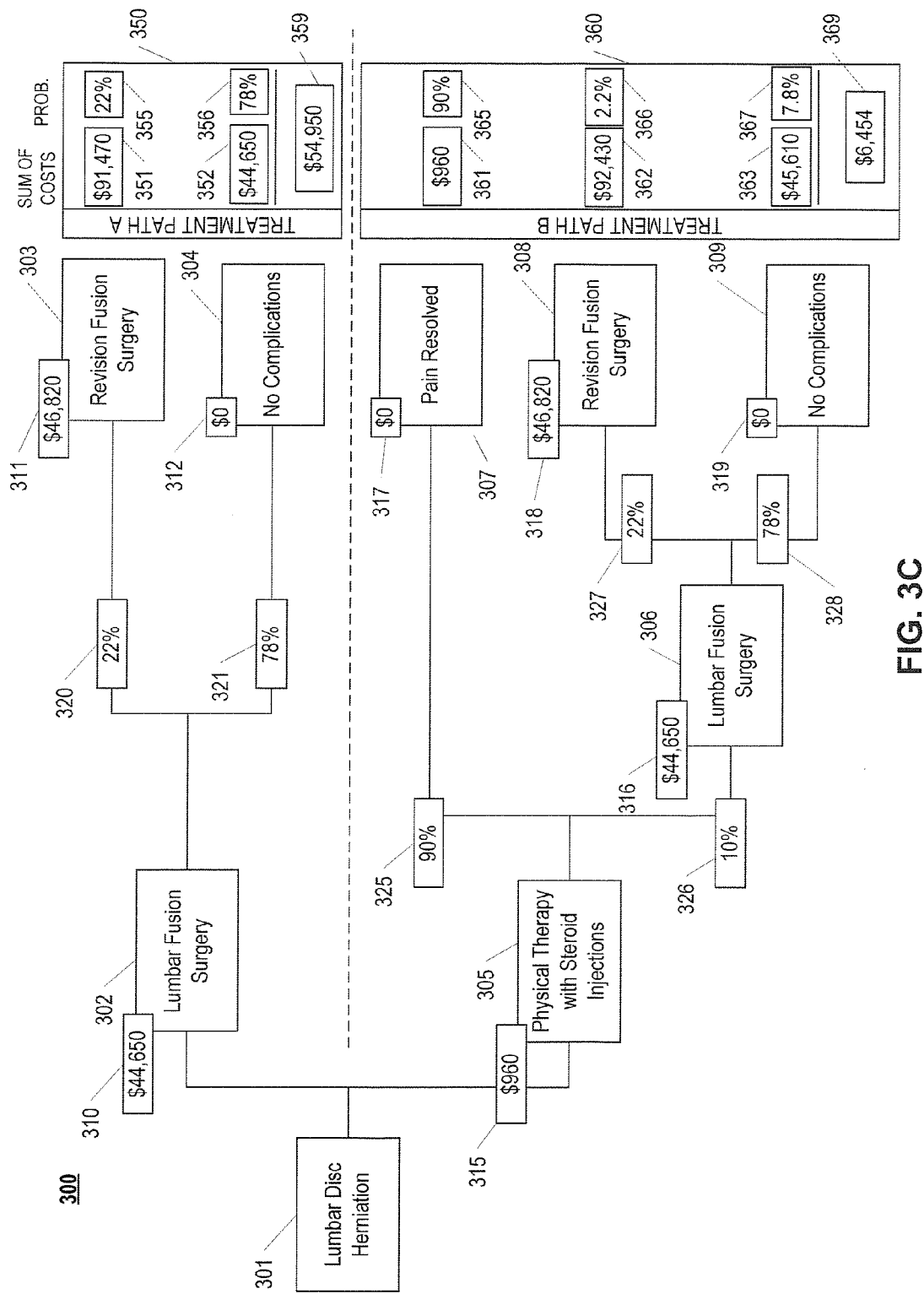

FIGS. 3A-3C are representations of an exemplary analytic model consistent with embodiments of the present disclosure. The analytic model 300 can be decision tree 300, similar to decision tree 200 of FIG. 2, that is directed to analyzing cost-effectiveness in a specific domain. Decision tree 300 can be directed to analyzing potential treatments of a medical procedure or condition to help determine the most cost-effective treatment.

FIG. 3A is an exemplary decision tree 300 representing an application of decision tree 200 of FIG. 2 to a specific domain. Decision tree 300 can be directed to treatment scenarios for lumbar disc herniation 301. Decision tree 300 can include multiple treatment paths for analysis. Lumbar fusion surgery 302 and physical therapy with steroid injections 305 are two potential treatment paths. Decision tree 300 can include as many or as few paths that exist for a particular scenario. Each potential treatment option (e.g., lumbar fusion surgery 302 or physical therapy with steroid injections 305) may lead to additional potential outcomes or events. For example, lumbar fusion surgery 302 can lead to a complication requiring revision fusion surgery 303 or can result in no complications 304. Either eventuality is a possibility.

Additional results of lumbar fusion surgery 302 can be included in decision tree 300. The potential outcomes are not limited to a complication requiring revision fusion 303 and no complications 304. Decision tree 300 can include all or none of the potential outcomes of each element under analysis. In some embodiments, decision tree 300 does not include revision fusion surgery 303 and no complications 304. In these embodiments, the analysis of lumbar fusion surgery 302 ends with lumbar fusion surgery 302. In some embodiments, additional complications, therapies, drug treatments, or other possible outcomes of lumbar fusion surgery 302 can be included for analysis. Mechanisms for choosing which potential outcomes to include in decision tree 300 are described in more detail below.

As shown in decision tree 300, lumbar fusion surgery 302 can lead to revision fusion surgery 303 and no complications 304. As an alternative to lumbar fusion surgery 302, decision tree 300 indicates that lumber disc herniation 301 can be treated by physical therapy with steroid injections 305. Physical therapy with steroid injections 305 can further result in pain resolved 307 or continued pain treated with lumbar fusion surgery 306. Lumbar fusion surgery 306, similarly to lumbar fusion surgery 302, can further result in revision fusion surgery 308 or in no complications 309.

As demonstrated in decision tree 300, branches in the tree can be duplicated within alternate treatment paths. For example, the branch consisting of lumbar fusion surgery 302 along with complications requiring revision fusion surgery 303 and no complications 304 are repeated as 306, 308 and 309. In this way, decision tree 300 can represent intervening steps (e.g., physical therapy with steroid injections 305) before proceeding with similar or the same branches existing in alternative paths (e.g., lumbar fusion surgery 302 and lumbar fusion surgery 306). In embodiments with duplicate branches, each event or element of the branch can be included in other relevant treatment paths. In some embodiments, the same procedure or event occurs in multiple treatment paths but the outcomes or events resulting from that procedure are not identical.

FIG. 3B is an exemplary decision tree 300 representing treatment scenarios for treating lumbar disc herniation 301 with the addition of probability and weight information. In some embodiments, such as those dealing with treatment scenarios, the weight information is represented by a cost associated with each option and outcome for a treatment. The included cost and probability information can be based on multiple data sources. In some embodiments, the cost and probability information can be based on a combination of multiple data sources or can be based on individual data sources. The manner for choosing appropriate data is discussed in more detail below.

Decision tree 300 can include cost information for each treatment scenario represented in decision tree 300. For example, lumbar fusion surgery 302 can be determined to cost $44,650 dollars based on available data. Decision tree 300 can include the amount on the decision tree in cost 310 and cost 316 associated with lumbar fusion surgery 302 and lumbar fusion surgery 306 respectively. Because these procedures are the same, the cost value for cost 310 and 316 will be the same. In some embodiments, cost estimates for the same procedure appearing in different treatment paths can differ depending on other circumstances in the specific treatment paths. For example, the available data can indicate that the effects of physical therapy with steroid injections 305 result in additional considerations that raise the cost of lumbar fusion surgery 306. In this example, cost 316 can be increased to account for the additional costs related to the associated procedure.

Decision tree 300 can further indicate that costs 311 and 318 of $46,820 are associated with revision fusion surgery 303 and 308 respectively, and costs 312 and 319 of $0 are associated with no complications 304 and 309 respectively. Further, decision tree 300 can associate cost 317 of $0 with pain resolved 307.

In addition to cost determinations, decision tree 300 can represent the probability that a certain treatment or event can occur. Similarly to the cost data, decision tree 300 can use multiple data for the probability information. Further, as with the cost data, decision tree 300 can combine data from multiple data sources or use individual data sources to arrive at a specific probability.

Each path in decision tree 300 represents an alternative treatment scenario. If lumbar fusion surgery 302 is chosen, probability 320 and 321 can indicate the relative probabilities of the outcomes of lumbar fusion surgery 302. Probability 320 can indicate that there is a 22% chance that after lumbar fusion surgery 302, revision fusion surgery 303 will occur. Similarly probability 321 can indicate that there is a 78% chance that no complications 304 will result from lumbar fusion surgery 302.

In representing physical therapy with steroid injections 305, decision tree 300 can include probability 325 indicating a 90% chance that physical therapy with steroid injections 305 can result in pain resolved 307. Further, probability 326 can indicate that there is a 10% chance that physical therapy with steroid injections 305 will result in lumbar fusion surgery 306. Similarly to probability 320 and 321, probability 327 can represent a 22% chance that lumbar fusion surgery will result in revision fusion surgery 308 and probability 328 can represent a 78% chance lumbar fusion surgery will result in no complications 309.

FIG. 3C is an exemplary decision tree 300 representing treatment scenarios for treating lumbar disc herniation 301 that includes individual cost and probability information as well as the weighted expected probability cost of each treatment path. Combining the probability and costs of each branch in each treatment scenario can result in a weighted cost estimate for each alternative treatment path.

Cost analysis 350 can represent the estimated cost of treating lumbar disc herniation 301 with lumbar fusion surgery 302. Cost analysis 350 can be based on a combination of all costs and probabilities contained within a particular treatment path.

Adding all costs associated with a particular branch of a treatment path can provide a total cost for that branch. For example, cost analysis 350 can represent the cost of lumbar fusion surgery 302 that requires revision fusion surgery 303 by adding cost 310 with cost 311 to result in a total branch cost 351 of $91,570. Further, lumbar fusion surgery 302 resulting in no complications 304 can result in a total branch cost 352 of $44,650, which can be determined by adding associated costs 310 of $44,650 and cost 312 of $0.

The probability that each of the two possible outcomes of lumbar fusion surgery can be represented by probability 320 and probability 321. Because probability 320 and 321 can represent the only probable outcomes following lumbar fusion surgery 302, these probabilities can be directly included in cost analysis 350. Branch probability 355 of 22% corresponds to probability 320 representing a 22% chance that revision fusion surgery 303 follows lumbar fusion surgery 302. Further, branch probability 356 corresponds to probability 321 representing a 78% chance that no complications 304 follow lumbar fusion surgery 302.

Cost analysis 350 can use cost estimates 351 and 352 with probabilities 355 and 356 to determine a weighted expected cost 359 for the treatment path beginning with lumbar fusion surgery 302. Cost analysis 350 can multiply cost estimate 351 of $91,570 with probability 355 of 22% to obtain a weighted, partial cost estimate of approximately $20,323 and can multiply cost estimate 352 of $44,650 with probability 356 of 78% to obtain a weighted, partial cost estimate of approximately $34,827. Summing these weighted partial costs that are associated with each possible branch of the treatment path can provide a weighted, total cost estimate 359 of $54,950 for treatment of lumbar disc herniation 301 with lumbar fusion surgery 302.

Similarly, cost analysis 360 can represent the estimated cost of treating lumbar disc herniation 301 with physical therapy with steroid injections 305. If physical therapy with steroid injections 305 results in pain resolved 307, the estimated cost of treatment can be the sum of cost 315 of $960 with cost 317 of $0 for an estimated cost 361 of $960. If physical therapy with steroid injections results in lumbar fusion surgery 306, further treatment possibilities of no complications 309 and revision fusion surgery 308 affect the cost estimates for cost analysis 360. The estimated cost 362 of the treatment path ending with revision fusion surgery can be obtained by adding the cost 315 of physical therapy with steroid injections, the cost 316 of lumbar fusion surgery 306, and cost 318 of revision fusion surgery 308. Accordingly, $960, $44,650, and $46,820 can result in an estimated branch cost 362 of $92,530. The estimated cost 363 for the treatment path ending with no complications 309 can be obtained by adding cost 315 of $960, cost 316 of $44,650, and cost 319 of $0. In this example, cost 363 is $45,610.

Cost analysis 360 can also determine the probabilities associated with each potential treatment branch that can result from physical therapy with steroid injections 305. As indicated probability 325 can represent that there is a 90% probability that physical therapy with steroid injections results in pain resolved 317. Because pain resolved 307 results in no additional treatment, the total estimated probability 365 for the treatment branch ending with pain resolved 307 can also be 90%.

As shown in FIG. 3C, treatment for lumbar disc herniation 301 with physical therapy with steroid injections 305 can possibly include lumbar fusion surgery 306 and either revision fusion surgery 308 or no complications 309. The treatment branch ending in revision fusion surgery 308 can result from a 10% probability 326 of lumbar fusion surgery 306 and a 22% probability 327 of revision fusion surgery 308. Multiplying probability 326 with probability 327 can yield an overall probability 366 of 2.2% that treatment of lumbar disc herniation 301 with physical therapy with steroid injections 305 results in revision fusion surgery 308. Similarly probability 328 can represent a 78% chance that lumbar fusion surgery 306 results in no complications 309. Multiplying probability 326 with 328 can yield an overall probability 367 of 7.8% that treatment of lumbar disc herniation 301 with physical therapy with steroid injections 305 results in no complications 309. It is appreciated that overall probabilities can be rounded up or down where appropriate. For example, overall probability 366 can be rounded to 2%, while overall probability 367 can be rounded to 8%.

As with cost analysis 350, cost analysis 360 can combine cost estimates 361, 362, and 363 with probabilities 365, 366, and 367 to produce a weighted, partial cost estimate 369 for treating lumbar disc herniation 301 using physical therapy with steroid injections 305. Multiplying cost estimate 361 of $960 by the probability 365 of 90% can result in a weighted cost estimate of approximately $864 for the treatment branch ending with pain resolved 307. Similarly multiplying cost estimate 362 of $92,530 with probability 366 of 2.2% can yield a weighted, partial cost estimate of approximately $2,033 for the treatment branch ending with revision fusion surgery 308. Finally, multiplying cost estimate 363 of $45,610 by probability 367 of 7.8% can result in a weighted, partial cost estimate of approximately $3,557. The sum of these weighted cost estimates can provide a total, weighted cost estimate 369 of $6,454 for treatment of lumbar disc herniation 301 using physical therapy with steroid injections 305.

After a total cost estimate is determined for each potential treatment option, the cost estimates can be compared to determine the most cost-effective treatment path. For example, decision tree 300 can demonstrate that lumbar fusion surgery 302 can have cost estimate 359 of $54,950 while treatment using physical therapy with steroid injections can have a cost estimate 369 of $6,461. Although both treatment options can possibly include lumbar fusion surgery (e.g., lumbar fusion surgery 302 or lumbar fusion surgery 306), decision tree 300 can reveal that, because of the probability factors, treatment using physical therapy with steroid injections 305 can drastically reduce the overall expected cost of treating lumbar disc herniation 301.

Figure 4:
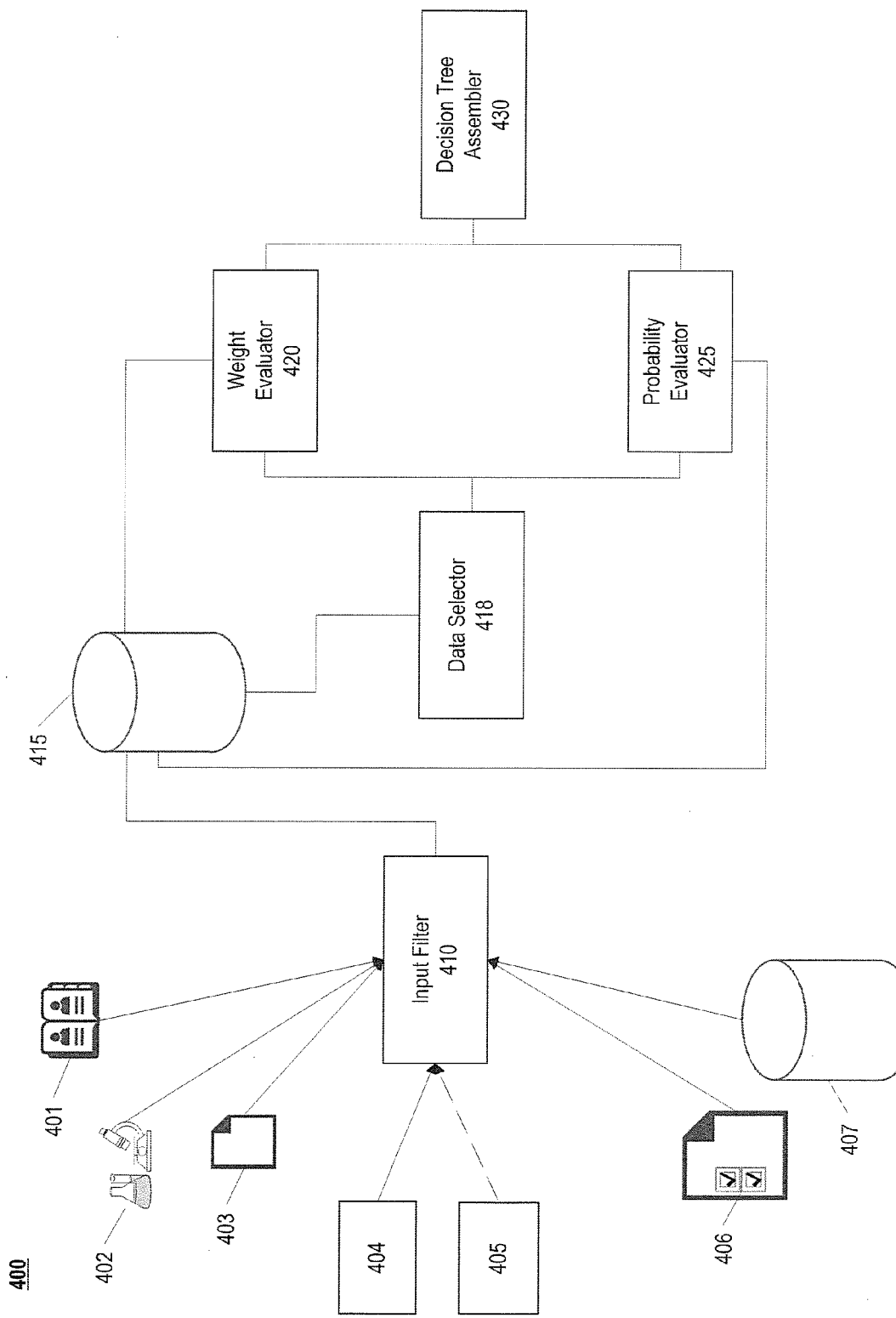
FIG. 4 is a block diagram representing an exemplary system for evaluating data sources, consistent with embodiments of the present disclosure.

FIG. 4 is a block diagram representing exemplary system 400 for evaluating data sources, consistent with embodiments of the present disclosure. System 400 can prepare a decision tree, which can be similar to the decision trees provided in FIG. 2 and FIGS. 3A-3C, for display on a display device similar to display device 124 in FIG. 1. System 400 can accept data sources (e.g., data sources 401-407), normalize and sanitize the data in those data sources (e.g., using input filter 410), store the data in storage 415, select a subset of the data (e.g., using data selector 418) according to the nature of the data, evaluate the data (e.g., using weight evaluator 420 and probability evaluator 425), and populate a decision tree for display (e.g., using decision tree assembler 430) based on the results of the respective evaluations. By intelligently analyzing potential data sources, system 400 can comb through an ever expanding corpus of available data to determine which sources and data are most relevant to the particular circumstances being analyzed.

The data can originate from a variety of sources. The data sources can include publicly available information, proprietary analysis or data sources, and privately held information. For example, data sources can include published journal articles (e.g., journal 401), research reports and documentation (e.g., research 402), and/or whitepapers or other published documents (e.g., document 403). While these examples can be publicly accessible, system 400 can also utilize private sources of information. For example system 400 can use data from, inter alia, internal databases (e.g., database 407), internally conducted surveys or polls (e.g., survey 406), and results from prior analysis. It is appreciated that the above mentioned sources are exemplary. Any source of information (including either public or private information) that can be accessed and can provide relevant data, can contribute to the corpus of data available to system 400. Data sources 404 and 405 can represent additional sources of data. The total number of sources can be smaller or larger than shown in FIG. 4.

Additionally, the data sources and the data provided by those sources can be dynamic. Data sources can continually be added, and data from those sources can be continually processed. As system 400 progresses, more data can be obtained and processed for later use.

Further, the data sources can be domain specific. Depending on the particular circumstances of system 400, certain types of data sources can be ignored or included. As an example, specific data sources for healthcare analysis can include, without limitation, administrative billing claims, third party vendors publishing average pricing benchmarks such as Healthcare Bluebook, Redbook, and PriceRX, published clinical studies or clinical trials, and health care practitioner (e.g., medical doctor) opinions and surveys.

Because of the diversity of the data and data sources provided by data sources 401-407, input filter 410 can be used. Input filter 410 is a module, which is a packaged functional hardware unit designed for use with other components or a part of a program that performs a particular function of related functions. In particular, input filter 410 processes the data provided by each data source before storing the data in data storage 415. Processing can include, inter alfa, normalizing the data to a consistent scale or baseline, sanitizing data to correct errors or differences in formatting, running an optical character recognition software to make data searchable, extracting keywords or identifiers, and classifying the data as related to pre-determined categories or classifications. Input filter 410 can use a variety of mechanisms to process the data depending on the format and nature of the data and/or data source. After processing the data, input filter 410 can store the data in data storage 415.

Data storage 415 can utilize one or more storage mechanisms based on any tangible and/or non-transitory storage or memory. This can include, but is not limited to, the types of memory and storage described in relation to FIG. 1. Further, data storage 415 can store the data in a variety of formats. For example, data storage 415 can be an object-relational database, a non-relational database, a full-text indexed data storage, and/or other database system.

Data selector 418 is a module configured to acquire data from data storage 415 for use by weight evaluator 420 and probability evaluator 425, which are also modules. Data selector 418 can consider the specific characteristics of the domain and circumstances under analysis and acquire relevant data from data storage 415 based on those considerations. Data selector 418 can determine weight data consisting of the data likely to be relevant to evaluating the weight or value associated with events, options, or outcomes (e.g., the events, options, and outcomes contributing to decision tree 200 from FIG. 2). Similarly, data selector 418 can determine probability data consisting of the data likely to be relevant to evaluating the probability that each event, option, or outcome under consideration will or can occur. Data selector 418 can retrieve the relevant data from data storage 415 and provide the weight data to weight evaluator 420 and probability data to probability evaluator 425. In some embodiments, the same data can be related to both weight and probability. In these embodiments, data selector 418 provides the data to both weight evaluator 420 and probability evaluator 425 for evaluation.

Weight evaluator 420 and probability evaluator 425 are modules that can analyze the data, determine which data sets can most effectively contribute to the decision tree analysis, and establish values for populating a decision tree. The evaluators can provide the determined values to decision tree assembler 430, which can produce a decision tree for display. Each evaluator can prioritize the input data based on a variety of criteria and evaluate that prioritized data to populate the appropriate sections of decision tree produced by decision tree assembler 430. Decision tree assembler 430 is a module that can acquire data from the evaluators, use the data to create a decision tree analysis, and prepare the decision tree for display. In determining which data should be prioritized and/or used, weight evaluator 420 and probability evaluator 425 can also consider the ease with which accurate values can be obtained from each data source.

The evaluators (e.g., weight evaluator 420 and probability evaluator 425) can decrease the relative priority for data that could have a lesser effect on the overall analysis and increase the relative priority for data that could have a larger effect on the decision tree analysis. Generally, weight data can be easier to prioritize than probability data because of the nature of the data, but the relative priority can ultimately depend on the specific circumstances of the analysis and the available data sources. Because the specific characteristics and details of weight data and probability data differ, weight evaluator 420 and probability evaluator 425 can use different methods and techniques for evaluating their respective categories of and data.

Weight evaluator 420 can examine weight data provide by data selector 418 to determine prioritization of the data and the ease with which accurate data can be obtained from the various data sources. Because weight data is often easily obtainable, much of the weight data may automatically be given a higher priority. For example, in a healthcare context, many treatments or procedures identified by, inter alia, established Current Procedural Terminology ("CPT®") codes, Healthcare Common Procedure Coding System ("HCPCS") codes, National Drug Code ("NDC") codes, or International Classification of Diseases ("ICD-9") codes, have weight details in the form of overall cost that can be readily obtained from insurance information and other public information. Because weight values are often easily obtainable from the various data sources, weight evaluator 420 can de-prioritize weight data that would require extensive analysis or calculation to retrieve an accurate weight value.

After prioritizing the weight data sets, weight evaluator 420 can further analyze the prioritized data to determine the most accurate values for use by system 400. This system can vary depending on the specific domain and nature of the data. As an example, a process that can be used by weight evaluator 420 to analyze healthcare related data will be described as an exemplary method for evaluating data.

In a healthcare environment, (e.g., the data and circumstances providing the basis for decision tree 300 in FIGS. 3A-3C), treatments or procedures can involve hundreds of potential services, each of which can be grouped under one or several different diagnostic codes. Weight evaluator 420 can account for the potential that some codes associated with the treatment or procedure can be excluded from a list of related procedures.

In this example, weight evaluator 420 can analyze a particular treatment to determine the appropriate diagnostic codes that can be utilized to determine a cost estimate for a treatment. For a treatment or procedure that can be billed under multiple diagnostic codes and/or code schemes, weight evaluator 420 can examine a large corpus of raw claims data to determine (e.g., calculate) actual patient costs occurring over a pre-specified number of days or weeks before and after the specific treatment. The pre-specified number of days or weeks can depend on the specific treatment, input from healthcare professional, or other sources of information that provide relevant details about the typical length of time needed for the treatment.

Further, weight evaluator 420 can identify the primary code related to the treatment. This identification can rely on past analysis or rely directly on input from a health care professional. After the primary code is identified, weight evaluator 420 can analyze other, secondary codes to determine the frequency at which those secondary codes occur within and outside of the chosen time period. If the frequency at which the secondary code occurs within the specified time period is more than a threshold amount over the frequency at which that secondary code occurs outside of the specified time period, weight evaluator 420 can consider the secondary code as related to the primary code and as contributing to the overall cost of treatment.

The specific threshold can be determined based on previous analysis or based on input provided directly by a healthcare professional who reviews the secondary code determinations to ensure that the identified codes are related. In some embodiments, weight evaluator 420 can instead use a formal statistical analysis to measure the degree to which secondary codes are related to the chosen primary code. As demonstrated in this example, throughout the evaluation process, probability evaluator can provide data from the analysis back to data storage 415 and request additional information from data storage 415 and data selector 418.

In the healthcare context, weight evaluator 420 can further account for errors that occur in including or excluding certain secondary diagnostic codes using the previously described system. Because errors are less meaningful if the overall cost of treatment is small, weight evaluator 420 can analyze the considered diagnostic codes to evaluate the average cost per patient for each code and the standard deviation across patients. If the average cost and standard deviations are below certain thresholds, weight evaluator can use the mean cost for that specific diagnostic code when calculating the total cost of the procedure. In some embodiments, weight evaluator considers any code having an average cost of less than $5,000 and a standard deviation of less than $2,000 as meeting the requirements for using the mean cost associated with the diagnostic code.

If the average cost or standard deviation for a specific diagnostic code exceeds the pre-determined thresholds, weight evaluator can obtain input from a qualified professional. In some embodiments, weight evaluator 420 triggers a review of any codes that account for at least a threshold percentage of the total cost associated with a treatment or procedure to ensure that each identified code requiring review is related to the primary diagnostic code. The specific percentage necessary can vary based on the specific treatment, the overall cost, embodiment specific preferences, or other criteria.

Moreover, weight evaluator 420 can standardize the cost assumptions for pharmacological treatments. If the mean annualized costs are below a given threshold (e.g., $5,000 in some embodiments), weight evaluator 420 can use the most common dosing regimen and mean number of prescription refills occurring across the corpus of data being considered. If the mean costs exceed the threshold, a patient specific estimate can instead be used. Weight evaluator 420 can use specific instructions from a patient's claim data or input provided by a medical professional to determine the recommended dosing regimen. In these cases, weight evaluator 420 still uses a mean number of prescription refills to account for the fact that actual medication compliance often falls short of a physician's recommended dosage.

Moreover, weight evaluator 420 can account for fluctuations in costs due to differences in traits of the patient (e.g., traits affecting treatments such as age, weight, medical history, etc.) geographic location, insurance coverage, and/or price inflation. Weight evaluator can adjust cost estimates based on known differences in these areas or pre-determined rules. In some embodiments, weight evaluator 420 can limit the data sources considered to those containing data with similar geographic, insurance, and inflation characteristics as the patient whose treatment is being analyzed by system 400.

As shown in the above example related to healthcare cost analysis, weight evaluator 420 can process the data provided by data selector 418 using a variety of different methods and techniques. This can include mechanisms to improve the data gathering, evaluate the accuracy of the data, rely on domain specific considerations, and account for errors that can occur because of the nature of the analysis.

In some embodiments, weight evaluator 420 further analyzes whether or not additional details are needed for a particular weight determination based on the overall impact that the data can have on the total weight of an option path (e.g., path 1 or path 2 as shown in FIG. 2) being analyzed by system 400. If the weight determination has little effect on the overall weight, weight evaluator 420 can accept the determined value without further analysis. If the weight determination does significantly affect the overall cost estimate, weight evaluator 420 can further analyze the determined values in an effort to improve the accuracy of the estimate.

To determine the significance of a particular weight determination to the overall weight of a path, weight evaluator 420 can apply a stochastic model to the produced decision tree. After probability estimates are determined as described below, weight evaluator 420 can provide weight distributions to decision tree assembler 430 representing potential weights for the decision tree. These distributions can be analyzed using a Monte Carlo method of statistical modeling (e.g., using software such as Oracle®'s Crystal Ball add-on to Microsoft® Excel) to generate an expected distribution of estimated total weight based on the individual weight distributions provided to decision tree assembler 430 by weight evaluator 420. In addition to the output distributions, the Monte Carlo analysis can also provide the mean variance in the overall weight resulting from each weight data source in the distribution indicating the effect of that particular data source on the final estimated weight. Weight evaluator 420 can determine if further analysis of a particular set of data is needed if the effect of that data is above a pre-determined threshold. In some embodiments, like those directed towards healthcare, weight evaluator 420 can request additional data directly from an expert physician to compare the determined value with published literature and trials and the physicians expertise to establish a conclusive value.

After weight evaluator 420 makes its determinations, weight evaluator 420 can provide the weight determinations to decision tree assembler 430 for inclusion in the decision tree analysis as described in FIG. 2 and FIG. 3A-3C.

Probability evaluator 425 performs similar functions as weight evaluator 420—analyzing the available data from data selector 418 to determine the individual priority and accuracy of each data set for use in providing probability determinations to decision tree assembler 430. While prioritization by weight evaluator 420 can be relatively trivial, prioritization by probability evaluator 425 can be much more essential to determining the relevant data for providing probability determinations Similar to weight evaluator 420, the specific methods used by probability evaluator 425 can be specific to the circumstances and domain of the data under consideration. For example, in examining the potential for a procedure or treatment to result in the recurrence of certain diseases, data indicating that the recurrence probability is in the range of 20%-40% must be considered a higher priority over data that indicate that the recurrence probability is in the range of 2%-4%. The former can have a much greater impact on potential treatment outcomes and results. Accordingly, probability evaluator 425 can ignore probabilities below a given threshold. For example, probability evaluator can ignore events that have less than a 2% chance of occurring. Conversely, data indicating higher probability ranges can be considered more relevant. The specific threshold used can be determined on a case by case basis depending on the specific domain and circumstances of the analysis.

In an effort to ensure correct prioritization of probability data, probability evaluator 425 can require additional information. This additional information can be gathered, processed by input filter 410, stored in data storage 415, and provided to probability evaluator 425 through data selector 418. For example, in a healthcare context, probability evaluator 425 can request surveys from physicians. Probability evaluator 425 can provide a brief description of treatment paths and a list of potential data sets containing probabilities. Probability evaluator 425 can obtain from the physicians polled, a list of the specific data sets each physician deems to be the most relevant to the treatment under analysis by system 400.

The methods used by probability evaluator 425 to make probability determinations can vary depending on the domain and circumstances of the analysis. The methods can further be driven by the nature of the data being analyzed. The following description of analysis in a healthcare context is exemplary and not intended to limit the disclosure to only healthcare applications.

In some embodiments, probability evaluator 425 can acquire physician recommendations related to the relevancy of the available data sets for making probability determinations. Probability evaluator 425 can analyze the physician responses provided through data selector 418 using a hypothesis test, such as a sequential probability ratio test ("SPRT") based on the SPRT developed by Abraham Wald and commonly used in manufacturing quality control tests. This method is well known in the field of statistical analysis. All physician responses related to a given probability determination can be tested using an SPRT. Probability evaluator 425 can establish a hypothesis that a particular data source is correct. The SPRT can establish, based on the responses, whether this hypothesis is true up to a certain confidence level, whether this hypothesis should be rejected in favor of an alternative hypothesis (e.g., that the particular probability is not correct), or whether additional responses are needed. If additional responses are needed, probability evaluator 425 can acquire the results of additional physician surveys and rerun the SPRT analysis after each response is obtained. The testing can continue until a conclusive decision is reached or until a specified number of physicians have been polled. Generally, if physician responses are similar, probability evaluator 425 can require fewer physician responses to make a conclusive determination. If physician responses are dissimilar, probability evaluator 425 can require a larger number of physician responses to reach a conclusive determination. Using the SPRT approach allows for a certain level of confidence to be reached while only requiring the number of responses necessary to reach that conclusion. Accordingly, the time and effort necessary to request additional physician responses that would add little to the analysis can be avoided.

After the SPRT is complete and use of a particular data set is verified, probability evaluator 425 can choose the mean value for that specific data based on the physician provided surveys. Probability evaluator 425 can ignore physician estimates falling more than a set number of standard deviations from the mean value.

Probability evaluator 425 can adjust constants that control the SPRT. These constants can allow probability evaluator 425 to balance the number of responses required with the level of confidence or certainty required to consider a probability input accurate. Probability evaluator 425 can adjust this balance depending on the nature of the data being considered and the physicians involved in the testing. If the importance of the probability data is relatively minor or the physicians have expert backgrounds in the particular area, probability evaluator 425 can favor reducing the number of responses required by placing less emphasis on the confidence level necessary to consider the produced values accurate. Conversely, if the input is of significant importance or the physicians polled have limited experience with the data, probability evaluator 425 can favor a higher level of confidence over reducing the number of required responses. In this way, probability evaluator 425 can consider the domain and data set to control the speed and thoroughness of the SPRT analysis.

Further, probability evaluator 425 can consider the range of probabilities being considered. Because data having smaller absolute probability values tend to result in less accurate estimates in physician polls, probability evaluator 425 can adjust the testing constants to favor higher levels of confidence when the absolute value of the probabilities being considered are small to account for the observed inaccuracy in small value estimates.

Instead of dynamically adjusting constants, in some embodiments, probability evaluator 425 chooses constants based on the results the constants produce. Probability evaluator can choose a set of constants, run an SPRT analysis, and compare the results to known data from clinical trials or studies. Although, the studies may not account for specific circumstances, similar results in the SPRT analysis to the general study can indicate that the constant values are effective in producing accurate results. In these embodiments, the constants chosen by this standardization process are then applied to specific probability data and circumstances of the event under analysis.

Similar to weight evaluator 420, probability evaluator 425 can analyze whether further testing is needed for a particular data set based on the overall impact that the data can have on the overall result of the analysis by system 400. If the data is insignificant to the overall cost, probability evaluator 425 can determine that no additional testing is necessary. If the input is significant to the overall result of decision tree assembler 430, probability evaluator 425 can further compare the determined values for the probability input with published literature or acquire a review from an expert.

To determine the significance of a particular data set to the overall result of the decision tree analysis, probability evaluator 425 can apply a stochastic model to the produced decision tree. After weight estimates are determined as described above, probability evaluator 425 can provide probability distributions to decision tree assembler 430 representing potential probability determinations. These distributions can be analyzed using the same Monte Carlo method used to apply stochastic models to the weight estimates. Probability evaluator 425 can generate an expected distribution of final weights based on the probability distributions provided to decision tree assembler 430. In addition to the output distributions, the Monte Carlo analysis can also provide the mean variance in the overall weights resulting from each probability data set distribution indicating the effect of that particular probability data set on the final estimated weight. Probability evaluator 425 can determine if further analysis of a particular data set is needed if the effect of a particular input is above a pre-determined threshold. In some embodiments in a healthcare context, probability evaluator 425 can acquire an expert comparison of the determined value to published literature and trials to establish a conclusive value.

After probability estimates are determined, probability evaluator 425 can provide the probability estimates to decision tree assembler 430 for inclusion in the decision tree analysis as described in FIG. 2 and FIGS. 2A-2C. After acquiring all weight and probability estimates, decision tree assembler 430 can prepare a decision tree for display on a display device similar to display device 124 in FIG. 1. Further, weight evaluator 420 and probability evaluator 425 can store the results of their analysis in storage 415 so that it can be used in subsequent analysis. In this way, system 400 can learn from its prior analyses providing increasingly accurate and efficient results.

In some embodiments, decision tree assembler 430 can provide the assembled data to other systems, components, or devices. These can be a computing device as described in FIG. 1 capable of receiving data from decision tree assembler 430 via network interface 118 or one or more of I/O devices 130. Further, these computing devices can store the information received from data assembler 430 in storage (e.g., storage 128) or memory (e.g., system memory 121 or graphic memory 126), further process the information (e.g., using CPU 120 or GPU 125), and/or display the information (e.g., using display device 124). These computing devices can be computers, mobile devices, or other systems that are communicatively coupled to system 400 either directly or in some other way such as a through a public or private network.

FIG. 5 is a flowchart of an exemplary method 500 for evaluating data sources and populating a decision tree (e.g., decision tree 200 in FIG. 2, decision tree 300 in FIGS. 3A-3C, and any decision tree provided by decision tree assembler 430 in FIG. 4). It will be readily appreciated that the illustrated procedure can be altered to delete steps or further include additional steps. After initial step 500, the system (e.g., system 400 from FIG. 4) can obtain (step 510) data sets associated with related events (e.g., event 201, options 1 and 2, and/or outcomes 1.1, 1.2, 2.1, 2.2, 2.2.1, and 2.2.2 in FIG. 2) from a variety of data sources (e.g., data sources 401-407). Data from the data sources can be in a variety of forms and related to one or more of the events being considered. In a healthcare context, this can include, but is not limited to, published journal articles, clinical trials, scientific studies, administered claims data, published cost information, insurance policy information, and/or opinions provided directly from experts. Further, data sources can include internal or proprietary databases or information systems. After obtained, the data can be, inter alia, sanitized, normalized, processed (e.g., by input filter 410 in FIG. 4), and stored in a database or other storage (e.g., data storage 415 in FIG. 4).

After obtaining the data, system can classify (step 520) the data as related to the weight of the events or as related to the probability of the occurrence of the events. As indicated during the discussion of FIG. 4, data can be identified as related to both weight and probability.

After classifying the data sets, system can prioritize (step 530) the identified weight data (e.g., using data evaluator 425 in FIG. 4). Weight data can be examined to determine if it provides weight information for the events under consideration. System can prioritize those data sets that contain clear weights associated with known values above those data sets that do not contain clear value information because of the ease with which weight estimates can typically be obtained from the data.

After establishing a prioritization for the weigh data, system can analyze (step 540) the data to determine weight estimates for the events being considered. The analysis can favor the more highly prioritized data. Depending on the domain, the analysis can rely on domain specific characteristics for the analysis. For example, in a healthcare context, system can account for treatments or procedures that may encompass multiple diagnostic codes by identifying a primary diagnostic code and analyzing the frequency with which other, secondary codes occur within a specified time period before and after the primary code. The specific time period can be chosen arbitrarily, based on known treatments for the primary code, or provided by an expert or physician familiar with the relevant procedure. In identifying secondary codes, system can analyze the primary and secondary codes obtaining a total cost for the treatment based on the prioritized documents. System can further account for potential codes that are incorrectly included or excluded by triggering a review of any identified codes that have a high average cost or that have costs that have large standard deviations from the average cost. Moreover, system can adjust the cost information provided by the cost data accounting for differences in geography, inflation, or insurance coverage between the patient or treatment under analysis and the treatment or patients in the cost data.

System can further evaluate which weight estimates need additional analysis by applying techniques such as stochastic modeling to the weight determinations. System can produce multiple decision trees using a distribution of potential weight estimates obtained from the prioritized data. By analyzing the resultant decision tree models, system can determine which weight estimates have the greatest effect on the overall result and require more detailed analysis of those particular data sets to increase the accuracy of the final estimate. Accordingly, system can determine which weight estimates are most important and direct resources and efforts into maximizing the accuracy of those estimates.

After classifying the data in step 520, system can prioritize (step 535) the identified probability data (e.g., using probability evaluator 425 in FIG. 4). In some embodiments, such as those directed to healthcare applications, system can acquire input from physicians and use statistical analysis techniques (e.g., SPRT as described in the discussion of FIG. 4) to prioritize data that provides the most relevant probability estimates for the events being considered. The parameters of the analysis can be chosen statically in an attempt to produce results consistent with generalized published studies (if available) or dynamically altered depending on the specific circumstances, probability data source, and/or experts involved.

After prioritization, system can analyze (step 545) the prioritized probability data sets to determine the appropriate probability estimates (e.g., using probability evaluator 425 in FIG. 4). In addition to using the most highly prioritized data, system can further analyze the data using tools such as stochastic modeling. In this process, system can produce decision trees representing a probability distributions obtained from the prioritized probability data sets. By analyzing the resultant decision trees, system can determine which probability estimates have the greatest effect on the overall weight. System can than analyze the data underlying those estimates in more detail to ensure a more accurate estimate. Accordingly, system can determine which probability estimates are more important and direct resources and efforts into maximizing the accuracy of those estimates.

System can use the estimates generated in steps 540 and 545 to populate (step 550) a decision tree. The populated decision tree can be similar to decision tree 200 from FIG. 2, and/or decision tree 300 from FIGS. 3A-3C. While intermediate decision trees can be generated during stochastic analysis of the weight and probability data sets, the result of those intermediate decision trees can inform the analysis in steps 540 and 545 resulting in a determination of more accurate values for populating the decision tree in step 550. The decision tree can then be used to investigate the result of various options or paths for responding to a particular event.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. An electronic device comprising:
a data storage configured to store one or more data sets associated with one or more resulting events wherein the one or more resulting events result from a first event;
a data selector configured to:
classify one or more of the one or more data sets as weight data sets, wherein the one or more weight data sets are related to weights associated with the one or more resulting events, and
classify one or more of the one or more data sets as probability data sets, wherein the one or more probability data sets are related to probabilities associated with an occurrence of the one or more resulting events;
a weight evaluator configured to determine one or more weight estimates for the one or more resulting events using a prioritization of the one or more weight data sets based on an availability of data within the one or more weight data sets; and
a probability evaluator configured to determine one or more probability estimates for the one or more resulting events using a prioritization of the one or more probability data sets based on an analysis of a relevance of the one or more probability data sets; and
a decision tree assembler configured to provide for display an analytical model including information based on the one or more weight estimates and the one or more probability estimates.

2. The electronic device of claim 1, wherein the weight evaluator is further configured to increase a priority of the one or more weight data sets wherein the one or more weight data sets include known values.

3. The electronic device of claim 1, wherein the weight evaluator is further configured to analyze the one or more weight data sets based on a statistical analysis of a primary diagnostic code associated with the event and one or more secondary diagnostic codes associated with the primary diagnostic code.

4. The electronic device of claim 1, wherein the weight evaluator is further configured to use a stochastic model to determine a significance of the one or more weight data sets to the one or more estimated weights related to the first event.

5. The electronic device of claim 1, wherein the probability evaluator is further configured to use a stochastic model to determine a significance of the one or more probability data sets to the one or more estimated weights related to the first event.

6. The electronic device of claim 1, wherein the relevance is based on a second data set.

7. A method performed by one or more processors and comprising:
obtaining one or more data sets associated with one or more events resulting from a first event;
classifying one or more of the one or more data sets as weight data sets, wherein the one or more weight data sets are related to weights associated with the one or more resulting events;
classifying one or more of the one or more data sets as probability data sets, wherein the one or more probability data sets are related to probabilities associated with an occurrence of the one or more resulting events;
determining one or more weight estimates for the one or more resulting events using a prioritization of the one or more weight data sets based on an availability of data within the one or more weight data sets;
determining one or more probability estimates for the one or more resulting events using a prioritization of the one or more probability data sets based on an analysis of a relevance of the one or more probability data sets; and
providing for display an analytical model including information based on the one or more weight estimates and the one or more probability estimates.

8. The method of claim 7, wherein prioritizing the one or more weight data sets includes increasing a priority of the one or more weight data sets wherein the one or more weight data sets include known values.

9. The method of claim 7, wherein determining the one or more weight estimates is partially based on a statistical analysis of a primary diagnostic code associated with an event and one or more secondary diagnostic codes associated with the primary diagnostic code.

10. The method of claim 7, wherein determining the one or more weight estimates further includes using a stochastic model to determine a significance of the one or more weight data sets to the one or more weight estimates.

11. The method of claim 7, wherein determining the one or more probability estimates further includes using a stochastic model to determine a significance of the one or more probability data sets to the one or more weight estimates.

12. The method of claim 7, wherein the relevance is based on a second data set.

13. A non-transitory computer readable storage medium storing instructions that are executable by a first computing device that includes one or more processors to cause the first computing device to perform a method for evaluating costs associated with a first event, the method comprising:
obtaining one or more data sets associated with one or more events resulting from a first event;
classifying one or more of the one or more data sets as weight data sets, wherein the one or more weight data sets are related to weights associated with the one or more resulting events;
classifying one or more of the one or more data sets as probability data sets, wherein the one or more probability data sets are related to probabilities associated with an occurrence of the one or more resulting events;
determining one or more weight estimates for the one or more resulting events using a prioritization of the one or more weight data sets based on an availability of data within the one or more weight data sets;
determining one or more probability estimates for the one or more resulting events using a prioritization of the one or more probability data sets based on an analysis of a relevance of the one or more probability data sets; and
providing for display an analytical model including information based on the one or more weight estimates and the one or more probability estimates.

14. The non-transitory computer readable medium of claim 13, wherein prioritizing the one or more weight data sets includes increasing a priority of the one or more weight data sets wherein the one or more weight data sets include known values.

15. The non-transitory computer readable medium of claim 13, wherein determining the one or more weight estimates is partially based on a statistical analysis of a primary diagnostic code associated with an event and one or more secondary diagnostic codes associated with the primary diagnostic code.

16. The non-transitory computer readable medium of claim 13, wherein determining the one or more weight estimates further includes using a stochastic model to determine a significance of the one or more weight data sets to the one or more weight estimates.

17. The non-transitory computer readable medium of claim 13, wherein determining the one or more probability estimates further includes using a stochastic model to determine a significance of the one or more probability data sets to the one or more weight estimates.

18. The non-transitory computer readable medium of claim 13, wherein the relevance is based on a second data set.

* * * * *

UNITED STATES PATENT AND TRADEMARK OFFICE
CERTIFICATE OF CORRECTION

PATENT NO. : 9,443,002 B1
APPLICATION NO. : 14/796946
DATED : September 13, 2016
INVENTOR(S) : Nate Freese et al.

Page 1 of 1

It is certified that error appears in the above-identified patent and that said Letters Patent is hereby corrected as shown below:

On the Title Page

Item [73], delete "Grand Rapids, Inc." and insert --Grand Rounds, Inc.--

Signed and Sealed this
Fifth Day of November, 2019

Andrei Iancu
*Director of the United States Patent and Trademark Office*